Figure 1:
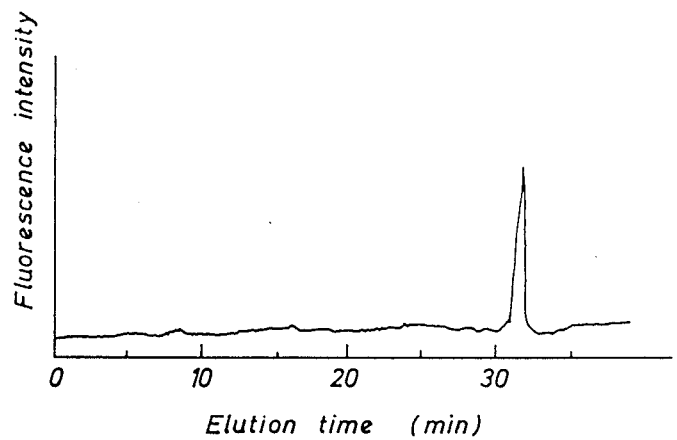

United States Patent [19]

Kondo et al.

[11] Patent Number: 4,975,533

[45] Date of Patent: Dec. 4, 1990

[54] METHOD FOR THE FLUORESCENT LABELLING OF SUGARS

[75] Inventors: Akihiro Kondo, Muko; Ikunoshin Kato; Akira Obayashi, both of Uji; Sumihiro Hase, Ashiya, all of Japan

[73] Assignee: Takara Shuzo Co., Ltd., Kyoto, Japan

[21] Appl. No.: 209,723

[22] Filed: Jun. 22, 1988

[30] Foreign Application Priority Data

Jul. 2, 1987 [JP] Japan .................. 62-163980

[51] Int. Cl.$^5$ .......................... C07H 1/00; C07H 5/06; C07H 17/02
[52] U.S. Cl. .................... 536/55.3; 536/1.1; 536/124; 436/546
[58] Field of Search ............ 536/55.3, 1.1, 124; 436/546

[56] References Cited

U.S. PATENT DOCUMENTS

| | | | |
|---|---|---|---|
| 4,432,907 | 2/1984 | Wieder et al. | 436/546 |
| 4,774,191 | 9/1988 | Khanna et al. | 436/518 |
| 4,801,504 | 1/1989 | Burdick et al. | 436/546 |

OTHER PUBLICATIONS

Her et al., J. Carbohydrate Chemistry, 6(1), 1987, pp. 129–139.
Reinhold et al., J. Carbohydrate Chemistry 2(1): 1–18 (1988).
Hase et al., Biochem. Biophys. Res Commun. 85(1): 257–263 (1978).
Hase et al., J. Biochem. 85:217–220 (1979).
Hase et al., J. Biochem. 90: 407–414 (1981).
Kosakai et al., J. Biochem. 92:295–303 (1982).
Hase et al., J. Biochem. 95:197–203 (1984).
Takemoto et al., Anal. Biochem. 145:245–250 (1985).
Tang et al., Carb. Res 136:259–271 (1985).
Coles et al., Carb. Res. 139:1–11 (1985).
Hase et al., J. Biochem. 90:1275–1279 (1981).

*Primary Examiner*—Ronald W. Griffin
*Assistant Examiner*—Nancy S. Carson
*Attorney, Agent, or Firm*—Armstrong, Nikaido, Marmelstein, Kubovcik & Murray

[57] ABSTRACT

A method for the fluorescent labelling of a sugar or a sugar chain by labelling the reducing end of the sugar or sugar chain with a fluorescent substance, wherein the improvement comprises first forming a Schiff base by reacting the surgar or sugar chain with the fluorescent substance in the presence of an acid which is substantially free from water, and second, reducing said Schiff base.

5 Claims, 2 Drawing Sheets

METHOD FOR THE FLUORESCENT LABELLING OF SUGARS

This invention relates to a method for the fluorescent labelling of a sugar or sugar chain, and particularly to a method for the quantitative fluorescent labelling of the reducing end of a sugar or sugar chain, so as to enable the analysis thereof with such a high sensitivity as the order of picomoles or better.

In recent years, the relationship between the physiological activities of conjugated sugars and the structures of their sugar chains has come to be studied, and further, differences in sugar chain structure and function between glycoproteins produced by the use of gene engineering technology and natural glycoproteins have also come to be studied. For these purposes and others it has come to be necessary to effect the analysis of the structures of sugars or sugar chains. However, living organisms usually produce only a small amount of such substance and hence only a slight amount of sample can be obtained thereof for testing. Therefore there is required a highly sensitive analytical method.

As methods for the analysis of trace amounts of sugar chains that are currently being used, there are those in which [$^3$H] label is introduced at the time of conversion of the reducing end into sugar alcohol and its radioactivity is utilized for the measurements (C. J. Liang, K. Yamashita, C. G. Muellenberg, H. Shichi, and A. Kobata, *J. Biol. Chem.*, 254, 6414 (1979), and S. Takasaki, T. Mizuochi, and A. Kobata, Methods in Enzymology, 83, 263 (1982)). The detection sensitivity is on the level of picomoles, which is satisfactory, but because the analysis involves the use of a radioactive substance, there are limitations in the use of the method. For that reason, a method for fluorescent labelling with the use of a pyridylamino group has been developed (S. Hase, T. Ibuki, and T. Ikenaka, *J. Biochem.*, 95, 197-203 (1984); hereinafter referred to as the 'conventional method'). In such conventional method, a pyridylamino group is introduced at the reducing end of a sugar or sugar chain by the use of hydrochloric acid to form a Schiff base, which is then reduced by the use of a nonvolatile boron compound. Then the sample is irradiated with an exciting wavelength of 320 nm, and the fluorescence at 400 nm is detected. The sensitivity is again on the level of picomoles.

If the above method is used, the analysis can be conducted with ease with the use of high-pressure liquid chromatography (HPLC), which is one of the most useful procedures in the field of microanalysis, and the sensitivity is equal to or greater than that achieved with the method that involves the use of a radioactive substance.

With the conventional method described above, however, the yield of the desired substance from the reaction in terms of the amount of the starting sugar or sugar chain is low, i.e. from 75 to 85%, which is not quantitative. Further, the yield of the reaction in the conventional method as applied to ketose is only about 10%, which is extremely unsatisfactory. Besides, with the conventional method, a large excess of 2-aminopyridine with respect to the starting sugar or sugar chain should be used to increase the Schiff base yield, and also, a large excess of sodium cyanoborohydride (NaBH$_3$CN) should be used as the reducing agent. Therefore, when the sugar or sugar chain that has been fluorescently labelled is to be analysed, the excess of 2-aminopyridine and NaBH$_3$CN must be removed by column chromatography, which requires both time and skill, and also detracts from the sensitivity of the analysis.

With these circumstances in mind, the object of this invention is to provide a method for fluorescent labelling in which the yield of the reaction for fluorescent labelling is improved, while the procedure is simplified, which method enables the microanalysis of sugar or sugar chain in a trace amount with sensitivity higher than that of previous methods.

Briefly, the invention relates to a method for the fluorescent labelling of sugar or sugar chain, in which there is used, as the counter ion, an acid substantially free from water, in the fluorescent labelling reaction at the reducing end of a sugar or sugar chain with a fluorescent substance having at least one amino group.

The sugars to which this invention may be applied are, for example, monosaccharides, oligosaccharides, polysaccharides, and conjugated sugars like glycoproteins or glycolipids. As methods by which the sugar chains can be cleaved from conjugated sugars like glycoproteins or glycolipids, there are well-known methods such as hydrazinolysis-N-acetylation, trifluoroacetolysis, alkali treatment, enzymatic digestion (endoglycosidase, glycopeptidase, etc.).

We have found that when hydrochloric acid, which has been used in the step of the reaction to form a Schiff base in the conventional method i.e. in the step of the reaction to introduce the fluorescent label, is replaced by an acid substantially free from water, for example, a substantially anhydrous inorganic acid (including an inorganic acid dissolved in an organic solvent, for example, hydrogen fluoride dissolved in pyridine) or an organic acid (for example, acetic acid, trifluoroacetic acid (TFA)), there can be obtain a far better result. Thus, for example, a sugar or sugar chain is reacted with an excess of a fluorescent substance having at least one amino group, (for example, 2-aminopyridine, 2-aminoquinoline, 2,3-diaminopyridine) in an acid which is substantially free from water.

Of the acids listed above, acetic acid is preferable, but other acids which do not contain water (for example, TFA) can also be used.

Standard reaction conditions are a temperature of from room temperature to 100° C. and a reaction time of several minutes to one hour. Preferably, the temperature is about 90° C. and the reaction time is about 15 minutes. In this reaction, Schiff bases are produced quantitatively, and the resulting reaction system may be purified by being concentrated and dried under reduced pressure and by azeotropic treatment.

For the reduction of said Schiff base, which is known per se, it is possible to use ordinary reducing agents for the Schiff bases, but borane complexes are particularly suitable. The ordinary kinds of borane complexes can be used, but for the sake of later steps, a borane complex that is volatile is preferred, of which the following examples can be named: borane-pyridine complex, borane-triethylamine complex, and borane-dimethylamine complex. The fluorescent substance which was used to form the Schiff base and the acid which is substantially free from water may be added to this reduction reaction system. The standard conditions for the reduction reaction are a temperature of room temperature to 100° C. and a reaction time of one hour to ten hours; preferably, the temperature is about 90° C. and the reaction time is about one hour. After the reaction, impurities may be removed by concentration of the reaction mixture under reduced pressure and by azeotropic treatment. Then the mixture is dissolved in an appropriate solvent and subjected to analysis by HPLC.

According to the method of this invention, the yield of the reaction for the fluorescent labelling is quantitative, even for aldose (inclusive amino sugars) and ketose, and when a volatile reagent is used, it can be removed with ease.

Figure 2:
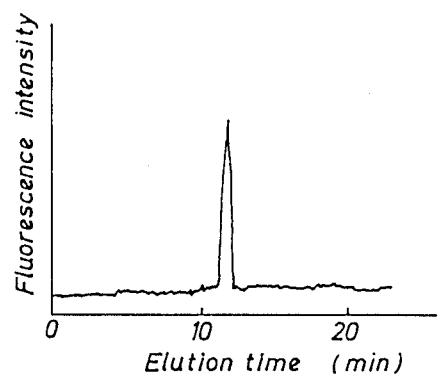
Figure 3:
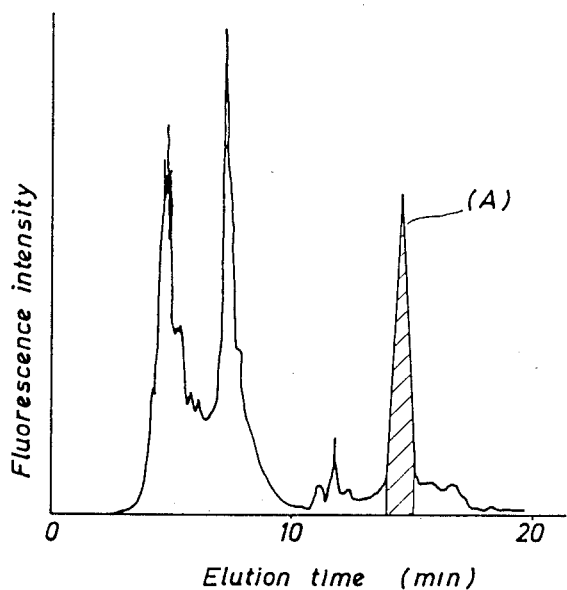

The invention will be concretely explained by means of the following Examples and by referring partly to the accompanying drawings wherein FIG. 1 and FIG. 2 show the results of analysis by HPLC chromatography of N-acetylglucosamine and fructose, both of which have been labelled fluorescently, respectively, and FIG. 3 shows the result of analysis by reverse-phase column chromatography of the fluorescent labelled fetuin.

The Examples are given for illustration purpose only and not for limiting the scope of the invention in any way.

EXAMPLE 1

Fluorescent labelling of N-acetylglucosamine

In 100 ml of water, 11.06 mg of N-acetylglucosamine (recrystallized from methanol; Wako Pure Chemical Industries, Ltd.) was dissolved. Then a 2-$\mu$l portion of this solution (which contained 1 nmol of N-acetylglucosamine) was put into a test tube and lyophilized to remove water. To the test tube, 10 $\mu$l of pyridylamination agent (23M solution of 2-aminopyridine in acetic acid) was added. The test tube was sealed and heated at 90° C. After 15 minutes, the test tube was opened, and excess reagents and the acetic acid were removed by azeotropic treatment with the use of triethylamine and concentration under reduced pressure. The residue was dissolved in 50 $\mu$l of methanol and 2 $\mu$l of borane-pyridine complex (Aldrich Chemical Co., Inc.) was added and the tube was sealed. Then the reduction reaction was carried out by keeping the test tube at 90° C. for one hour. After the reaction, the tube was opened, and the reagents and solvent were removed by concentration under reduced pressure and azeotropic distillation. The residue was dissolved in 200 $\mu$l of water, and 2 $\mu$l of this solution (corresponding to 10 pmol) was analyzed by HPLC by the method of H. Takemoto, S. Hase, and T. Ikenaka (*Anal. Biochem.*, 145, 245 (1985)). FIG. 1 shows the chromatogram as showing the relationship between the elution time (minutes, abscissa) and the fluorescence intensity (ordinate). Incidentally, Ultrasphere $C_{18}$ column (4.6×250 mm, Beckman Instruments, Inc.) was used, with 0.025M sodium citrate buffer (pH 4.0) containing 0.1% acetonitrile as solvent, and a flow rate of 0.8 ml/minute. The area of the peak obtained was used for the calculation of the yield of fluorescent labelling, which was 94.1%.

EXAMPLE 2

Fluorescent labelling of fructose

First, 9.01 mg of fructose (Wako) was measured and dissolved in 100 ml of water. Of this solution, 2 $\mu$l (containing 1 nmol of fructose) was put into a test tube. The same procedures as in Example 1 for N-acetylglucosamine were repeated and the analysis was also done in the same way. The result of the analysis is shown in FIG. 2. The yield of the fluorescent labelling reaction was obtained from the area of this peak. The yield of fluorescent labelling was 92.3%.

EXAMPLE 3

Analysis of the sugar chains of fetuin (glycoprotein from calf fetal serum)

(1) Isolation of the sugar chains of fetuin

By the usual methods, 480 $\mu$g (1 nmol) of fetuin (Sigma Chemical Co.) was hydrazinolyzed and then N-acetylated as described by S. Hase, T. Ikenaka, and Y. Matsushima (J. Biochem., 90, 407–414 (1981)) and by S. Takasaki, T. Mizuochi, and A. Kobata (*Methods in Enzymol.*, 83, 263 (1982)). The reaction mixture containing the sugar chains and decomposed protein was lyophilized. This lyophilized substance was added with 45 $\mu$l of methanol and 5 $\mu$l of a 5M 2-aminopyridine solution in acetic acid. The solution was allowed to react at 90° C. for 15 minutes. Then the solvent was distilled off, and unreacted 2-aminopyridine was removed by four times of azeotropic distillation with triethylamine. To the residue, 50 $\mu$l of methanol was added for dissolution, after which 2 $\mu$l of borane-pyridine complex (Aldrich) was added. The test tube was sealed, and the reduction reaction was allowed to take place for 1 hour at 90° C. After the reaction, the solvent and the reagents were removed by azeotropic distillation. The residue obtained was analyzed by a well-known method (S. Hase, K. Okawa, and T. Ikenaka, *J. Biochem.*, 91, 735 (1982)) for HPLC with a reverse-phase column (Cosmosil $C_{18}$ (Nakarai Chemicals, Ltd.), 4.6×250 mm). As the solvent, 0.1M ammonium acetate buffer (pH 4.0) was used in a gradient of 0% to 0.5% n-butanol, and separation was done, resulting in sugar chain A, which were identified by both enzymatical and instrumental analysis. FIG. 3 shows the results of analysis of that chromatography in the same way as in FIG. 1. From the elution time, sugar chain A seemed to have a complex structure.

(2) Component analysis of the sugar chain A obtained from fetuin

The sugar chain A obtained as shown above in section (1) was hydrolyzed by the two kinds of methods described below. Each of the products was labelled fluorescently by the use of 2-aminopyridine and then analyzed.

(a) Analysis of neutral sugars

First, 100 pmol of sugar chain was dissolved in 60 $\mu$l of a 4M aqueous solution of TFA, and hydrolysis was allowed to proceed for 3 hours at 100° C. The reaction liquid was concentrated under reduced pressure and the residue was dissolved in 200 $\mu$l of a 10% solution of pyridine in methanol. To this mixture, 10 $\mu$l of anhydrous acetic acid was added, and the mixture was left to stand at room temperature for several minutes. Then the pressure was decreased to $10^{-3}$ torr, and concentration to dryness was conducted. The residue was dissolved in 45 $\mu$l of methanol. To this, 5 $\mu$l of 5M 2-aminopyridine in acetic acid was added, and the mixture was allowed to react at 90° C. for 15 minutes. This reaction liquid was concentrated and dried under a reduced pressure of $10^{-3}$ torr, and then the 2-aminopyridine that had not reacted was removed by four times of azetropic distillation with triethylene. The residue was dissolved in 50 $\mu$l of methanol and to this solution, 2 $\mu$l of boranepyridine complex was added. The test tube was sealed and the mixture was allowed to react for 1 hour at 90° C. Then, the reaction liquid was concentrated and dried under a reduced pressure of $10^{-3}$ torr, and azeotropic distillation was conducted repeatedly. The residue obtained was analysed by a well-known method (H. Takemoto, S. Hase, and T. Ikenaka, *Anal. Biochem.*, 145, 245 (1985)). The results are shown in Table 1.

(b) Analysis of amino sugars

First, to 100 pmol of sugar chains were added 20 μl of 6M HCl, 20 μl of 6M TFA, and 20 μl of water, and the mixture was hydrolyzed for 6 hours at 100° C. The procedures that followed were the same as those in section (a) above. The results are shown in Table 1. Table 1 also shows the results of analysis of the neutral sugars and amino sugars with correction of data (shown as mol/mol sugar chain) by use of the internal standard rhamnose.

TABLE 1

| Sample | Man | Gal | GlcNAc |
|--------|-----|-----|--------|
| (A)    | 2.7 | 3.2 | 5.3    |

Note:
Gal: galactose
GlcNAc: N-acetylglucosamine
Man: mannose

From the above results the structure of the sugar chain (A) of interest seemed to be as follows, corresponding to the major sugar chain structure of fetuin.

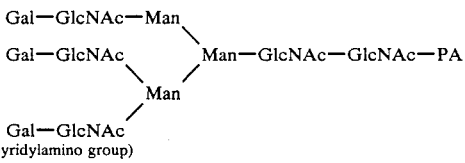

(PA: pyridylamino group)

As explained in detail above, by the method of this invention, it is possible to label sugar or sugar chain fluorescently in a quantitative reaction, and by the use of a volatile solvent, the procedure is simplified, making it possible to effect microanalysis of a trace amount of sugar or sugar chain.

What we claim is:

1. In a method for the fluorescent labelling of a sugar or a sugar chain comprising attaching a fluorescent ligand, comprising at least one amino group, to said sugar or sugar chain at its reducing end in the presence of an acid counter ion to form a Schiff base, the improvement which comprises first reacting said sugar or sugar chain with said ligand in the effective presence of said acid substantially free of water to form said Schiff base; and, in a second distinctly separate step, reducing said Schiff base.

2. A method as claimed in claim 1 wherein the acid is an anhydrous acetic acid or trifluoroacetic acid.

3. A method of claimed as claim 1 wherein the fluorescent ligand is 2-aminopyridine, 2-aminoquinoline or 2,3-diaminopyridine.

4. A method as claimed in claim 1 wherein said Schiff base formed by the reaction of said sugars is reduced by reaction with a volatile borane complex.

5. A method as claimed in claim 4 wherein the volatile borane complex is borane-pyridine complex, borane-triethylamine complex or borane-dimethylamine complex.

* * * * *